(12) United States Patent
Ben Dor et al.

(10) Patent No.: US 11,622,691 B2
(45) Date of Patent: Apr. 11, 2023

(54) OPTICAL PROBE FOR OXIMETRY MEASUREMENTS

(71) Applicant: Infrascan Inc., Philadelphia, PA (US)

(72) Inventors: Baruch Ben Dor, Radnor, PA (US); David Solt, Fort Washington, PA (US); Leonid Zubkov, Feasterville, PA (US)

(73) Assignee: INFRASCAN INC., Philadelphia, PA (US)

( * ) Notice: Subject to any disclaimer, the term of this patent is extended or adjusted under 35 U.S.C. 154(b) by 255 days.

(21) Appl. No.: 16/633,460

(22) PCT Filed: Aug. 24, 2018

(86) PCT No.: PCT/US2018/047913
§ 371 (c)(1),
(2) Date: Jan. 23, 2020

(87) PCT Pub. No.: WO2019/040849
PCT Pub. Date: Feb. 28, 2019

(65) Prior Publication Data
US 2020/0229712 A1    Jul. 23, 2020

Related U.S. Application Data

(60) Provisional application No. 62/549,978, filed on Aug. 25, 2017.

(51) Int. Cl.
*A61B 5/02* (2006.01)
*A61B 5/00* (2006.01)
*A61B 5/1455* (2006.01)

(52) U.S. Cl.
CPC ........ *A61B 5/02042* (2013.01); *A61B 5/0075* (2013.01); *A61B 5/14552* (2013.01);
(Continued)

(58) Field of Classification Search
CPC .............. A61B 5/02042; A61B 5/0075; A61B 5/14552; A61B 2560/045; A61B 2562/0233; A61B 2562/185; A61B 5/145
See application file for complete search history.

(56) References Cited

U.S. PATENT DOCUMENTS 5,482,034 A * 1/1996 Lewis ................ A61B 5/14552
356/41
6,174,424 B1  1/2001 Wach et al.
(Continued)

FOREIGN PATENT DOCUMENTS

CN    104434034 A    3/2015
CN    204233134 U    4/2015
(Continued)

OTHER PUBLICATIONS

Petrov, et al. Optoacoustic detection of intra- and etracranial hematomas in rats after blast injury. Photoacoustics. Apr. 13, 2014. [Retrieved on Oct. 13, 2018]. Retrieved from Internet: <https://ac/els-cdn.com/S221359791400010X/1-s2.0-S221359791400010X-main.pdf?_tid=7407550e-2c2f-4a1c-a6ee-38c3c339fe38&acdnat=1539699604_907e9c01914a06ab54d5743be7d26dc2> pp. 75-80.

(Continued)

*Primary Examiner* — Eric F Winakur
*Assistant Examiner* — Abid A Mustansir
(74) *Attorney, Agent, or Firm* — Morgan, Lewis & Bockius LLP

(57) ABSTRACT

An optical probe comprises three optical elements including at least one light source and at least one light detector. The three optical elements are positioned in a triangular configuration. Three optical fibers are each coupled to one of the three optical elements and have an exposed distal end portion. At least one light shroud is disposed radially around (Continued)

the exposed distal end portions of at least one of the optical fibers coupled to the at least one light source.

22 Claims, 18 Drawing Sheets

(52) U.S. Cl.
CPC .... *A61B 5/14553* (2013.01); *A61B 2560/045* (2013.01); *A61B 2562/0233* (2013.01); *A61B 2562/185* (2013.01)

(56) References Cited

U.S. PATENT DOCUMENTS

| | | | |
|---|---|---|---|
| 6,416,234 B1 | 7/2002 | Wach et al. | |
| 7,339,657 B2 | 3/2008 | Coates | |
| 8,060,189 B2 | 11/2011 | Ben Dor et al. | |
| 8,792,951 B1 | 7/2014 | Mao et al. | |
| 2004/0201835 A1* | 10/2004 | Coates | G01N 21/552 |
| | | | 356/73 |
| 2008/0183055 A1* | 7/2008 | Ninomiya | A61B 5/0059 |
| | | | 600/310 |
| 2008/0319290 A1* | 12/2008 | Mao | A61B 5/14552 |
| | | | 600/323 |
| 2009/0221919 A1* | 9/2009 | Ben Dor | A61B 5/0059 |
| | | | 600/473 |
| 2013/0289414 A1 | 10/2013 | Adibnazari et al. | |
| 2016/0296154 A1* | 10/2016 | Riley | A61B 5/725 |
| 2018/0110421 A1* | 4/2018 | Stratis | A61B 5/7282 |

FOREIGN PATENT DOCUMENTS

| | | |
|---|---|---|
| CN | 106491162 A | 3/2017 |
| WO | 2005/010568 A2 | 2/2005 |
| WO | 2016149827 A1 | 9/2016 |

OTHER PUBLICATIONS

International Search Report dated Nov. 19, 2018 for International Patent Application No. PCT/US2018/047913, 2 pages.
Written Opinion dated Nov. 19, 2018 for International Patent Application No. PCT/US2018/047913, 6 pages.
Chinese Notification of First Office Action dated Dec. 23, 2021 for Chinese Application No. 201880053478.7, 11 pages.
Search Report issued in corresponding Chinese Patent Application No. 2018800534787 dated Dec. 16, 2021.
Office Action issued in corresponding Chinese Patent Application No. 2018800534787 dated May 18, 2022, with English translation.
Office Action issued in corresponding Chinese Patent Application No. 2018800534787 dated Nov. 3, 2022, 7 pages.

* cited by examiner

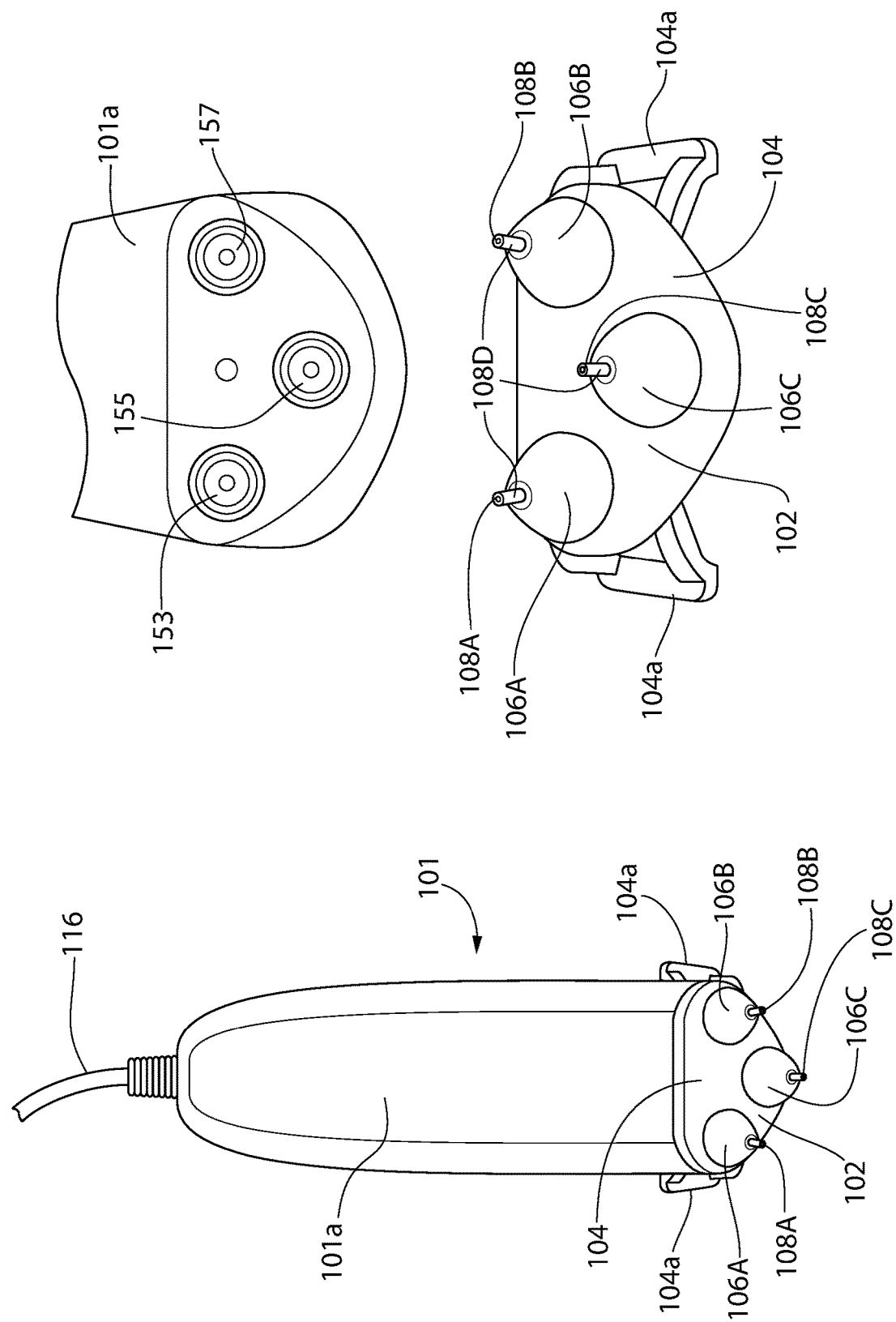

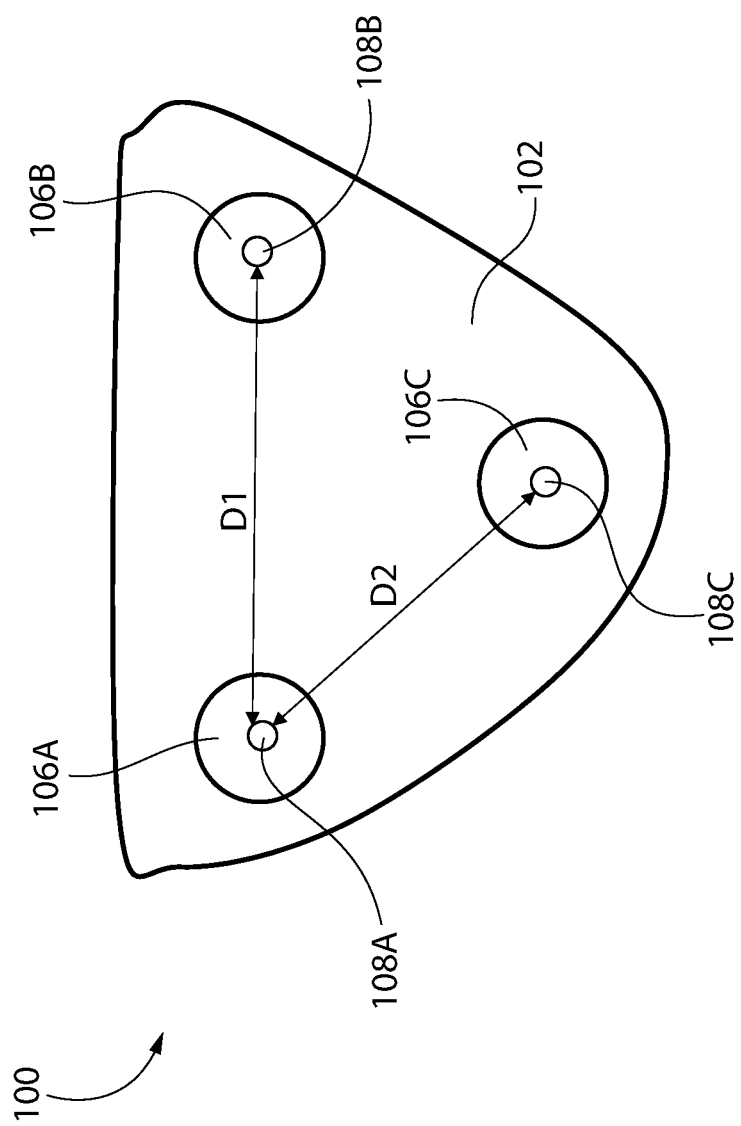

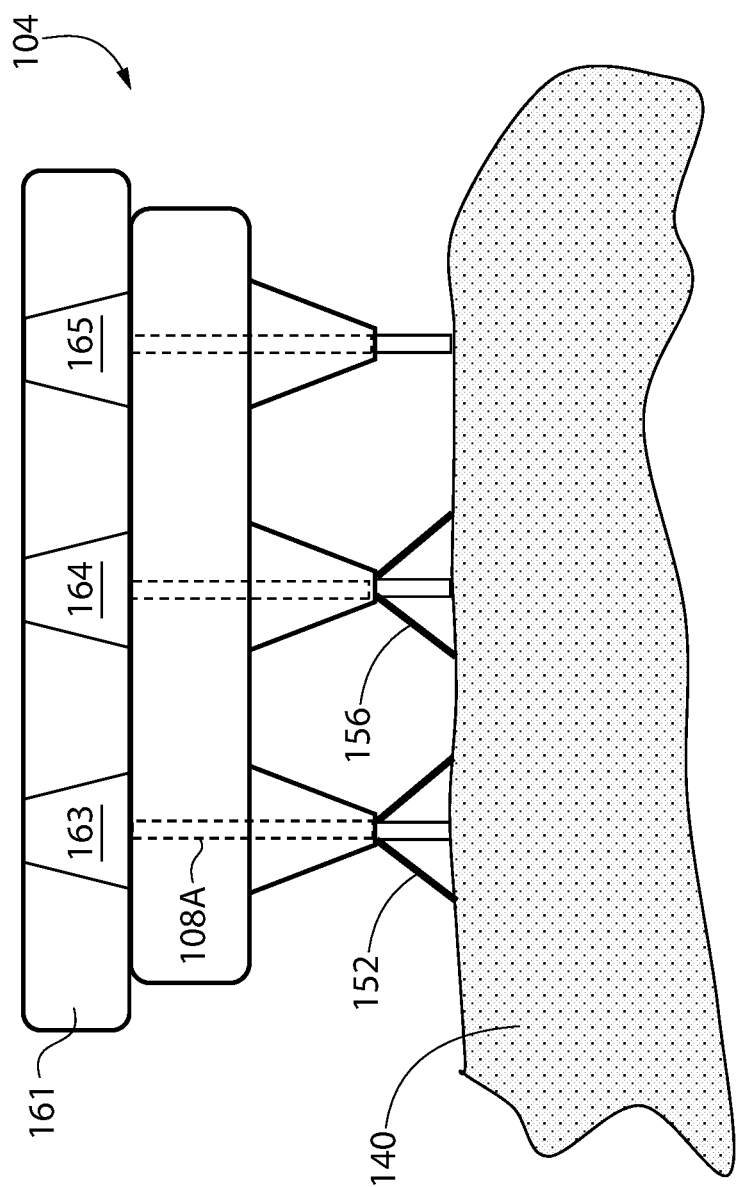

OPTICAL PROBE FOR OXIMETRY MEASUREMENTS

CROSS REFERENCE TO RELATED APPLICATIONS

This application is a U.S. National Stage Application of International Patent Application No. PCT/US2018/047913 filed Aug. 24, 2018 entitled "Optical Probe For Oximetry Measurements", which claims the benefit of U.S. Provisional Patent Application No. 62/549,978 filed Aug. 25, 2017 entitled "Multifunction Patient Triage System", each of which are incorporated by reference herein in their entirety.

GOVERNMENT FUNDING

This invention was made with government support under Contract No. W911QY-14-C-0082 awarded by the U.S. Marine Corps. The government has certain rights in the invention.

FIELD OF THE INVENTION

The present application generally relates to optical probes for oximetry measurements and, more particularly, to handheld optical probes for detection of hematomas.

BACKGROUND

One of the most important principles for the initial resuscitation of a head trauma patient is to promptly identify and surgically evacuate traumatic intracranial hematomas. Hematoma is a condition by which blood accumulates outside blood vessels, generally as a result of a hemorrhage or trauma. Such hematomas are often caused by a head injury, such as from a fall, motor vehicle collision, or an assault. The sudden blow to the head damages blood vessels that run along the surface of the brain.

Oximetry techniques can be used to assess amounts of oxygenated and deoxygenated blood in a patient. Oxygenated hemoglobin absorbs more infrared light and allows more red light to pass through. Deoxygenated (or reduced oxygen) hemoglobin absorbs more red light and allows more infrared light to pass through. Thus, by measuring differences in lights of various wavelengths, an oximetry measurement can be performed. The oximetry measurement can be used to assess head trauma injuries. In many cases, head trauma injuries are time critical, and thus, the ability to diagnose them at the scene of the injury using portable equipment is desirable. This allows the appropriate care to be administered as quickly as possible, improving the opportunity to save lives and reduce recovery times. An optical probe can be used for such measurements. U.S. Pat. No. 8,060,189 entitled System and Method for Detection of Brain Hematoma, which is hereby incorporated by reference as if set forth in its entirety herein, describes systems and methods of using oximetry measurement for detection of brain hematoma using near infrared spectroscopy. Disclosed herein are improvements in oximetry measurements using an optical probe.

BRIEF SUMMARY OF THE INVENTION

In one embodiment there is an optical probe comprising: three optical elements including at least one light source and at least one light detector, the three optical elements being positioned in a triangular configuration; three optical fibers each coupled to one of the three optical elements and having an exposed distal end portion; at least one light shroud disposed radially around the exposed distal end portions of at least one of the optical fibers coupled to the at least one light source.

In a further embodiment, the optical probe further comprises a base housing the three optical elements; and a cover removably coupled to a distal end of the base, the cover including the three optical fibers. In one embodiment, the cover includes three bosses, each boss projecting from the cover and covering a portion of one of the three optical fibers. In one embodiment, each boss is frusto-conical in shape. In one embodiment, the cover includes at least one flexible tab extending laterally from the cover and configured to snap fit onto the base. In one embodiment, the three optical elements include a first light source, a second light source, and a light detector. In one embodiment, the at least one light shroud includes a first light shroud disposed around the exposed tip of one of the optical fibers coupled to the first light source and a second light shroud disposed around the exposed tip of one of the optical fibers coupled to the second light source. In one embodiment, the first light source is disposed at a first distance from the light detector, and wherein the second light source is disposed at a second distance from the light detector, and wherein the first distance is greater than the second distance.

In one embodiment, the three optical elements include a first light detector, a second light detector, and a light source. In one embodiment, the first light detector is disposed at a first distance from the light source, and wherein the second light detector is disposed at a second distance from the light source, and wherein the first distance is greater than the second distance. In one embodiment, the first light detector is configured to allow for measurement of extracranial hematomas and the second light detector is configured to allow for measurement of intracranial hematomas.

In one embodiment, the three optical fibers are generally parallel to one another. In one embodiment, each of the three optical fibers extend at an angle towards a central point between the three optical fibers. In one embodiment, the at least one light shroud is cylindrically shaped. In one embodiment, the at least one light shroud is frusto-conically shaped. In one embodiment, the at least one light shroud includes a light-absorbing member disposed on an inside surface of the at least one light shroud comprised of a material different than a material of the remainder of the at least one light shroud.

In another embodiment, there is an optical probe comprising: a base housing three optical elements including at least one light source and at least one light detector, the three optical elements being positioned in a triangular configuration; a cover removably coupled to the base and including three optical fibers each coupled to one of the three optical elements having an exposed distal tip, the cover including three bosses, each boss projecting from the cover and covering a portion of one of the optical fibers; and at least one light shroud coupled to a distal end of one of the three bosses and disposed around the exposed tip of one of the optical fibers.

BRIEF DESCRIPTION OF THE SEVERAL VIEWS OF THE DRAWINGS

The foregoing summary, as well as the following detailed description of embodiments of the optical probe for oximetry measurements, will be better understood when read in conjunction with the appended drawings of exemplary embodiments. It should be understood, however, that the invention is not limited to the precise arrangements and instrumentalities shown.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity. Furthermore, for clarity, some reference numbers may be omitted in certain drawings.

In the drawings:

FIG. 1 is a schematic view of a diagnostic system shown during use on a patient in accordance with an exemplary embodiment of the present invention;

FIG. 2A is a bottom view of an optical probe shown in FIG. 1;

FIG. 2B is an exploded bottom view of the optical probe shown in FIG. 2A with the cover removed from the remainder of the optical probe;

FIG. 2C is a top view of the optical probe shown in FIG. 2A;

FIG. 2D is a side view of the optical probe shown in FIG. 2A;

FIG. 3A is a top view of a cover in accordance with alternative embodiments of the present invention;

FIG. 3B is a side view of the cover of FIG. 3A;

FIG. 4 is side view of an optical probe in accordance with an exemplary embodiment of the present invention illustrating of interference between optical elements;

FIG. 5A is a side view of the optical probe of FIG. 4 having a cylindrical shroud in accordance with embodiments of the present invention;

FIG. 5B shows a top view of the cylindrical shroud shown in FIG. 5A;

FIG. 6 is a side view of the optical probe of FIG. 4 having two cylindrical shrouds in accordance with embodiments of the present invention;

Figure 4:
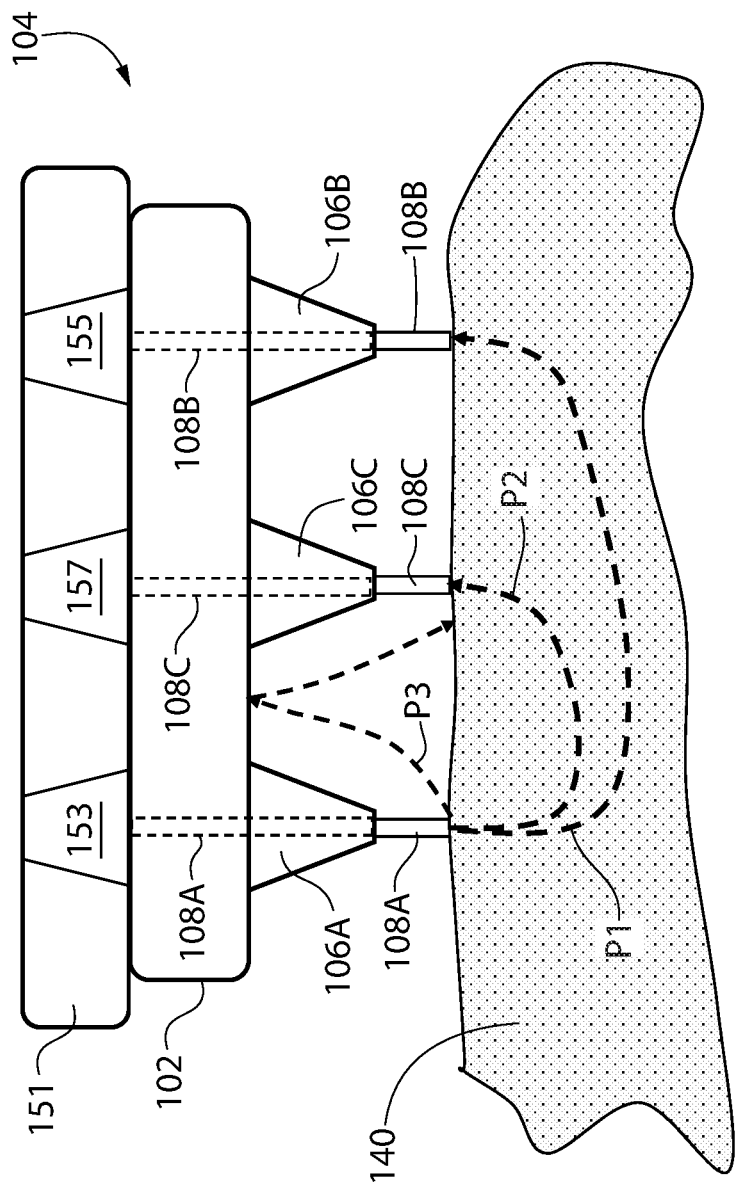
Figure 7B:
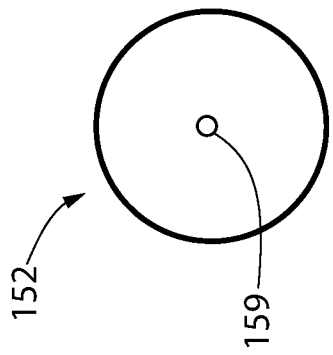
Figure 7A:
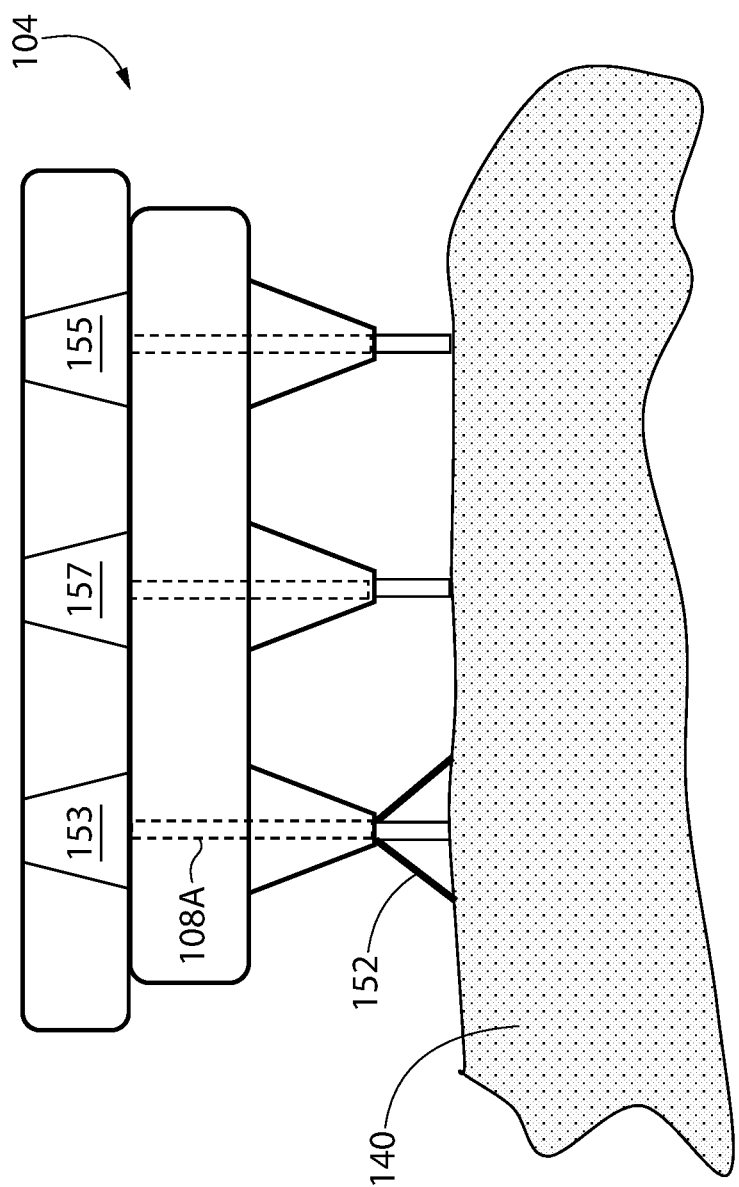
Figure 9:
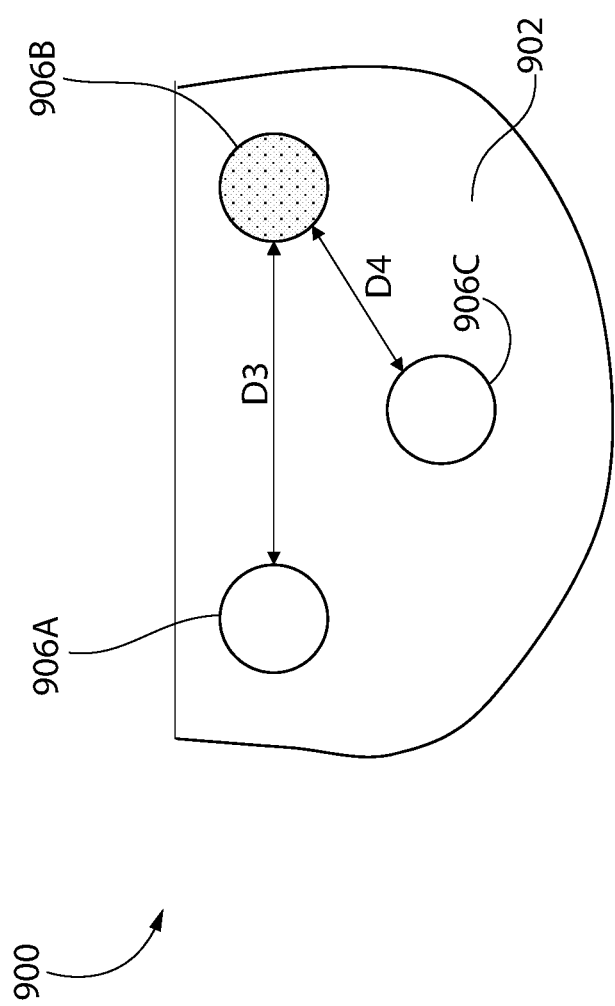
Figure 10:
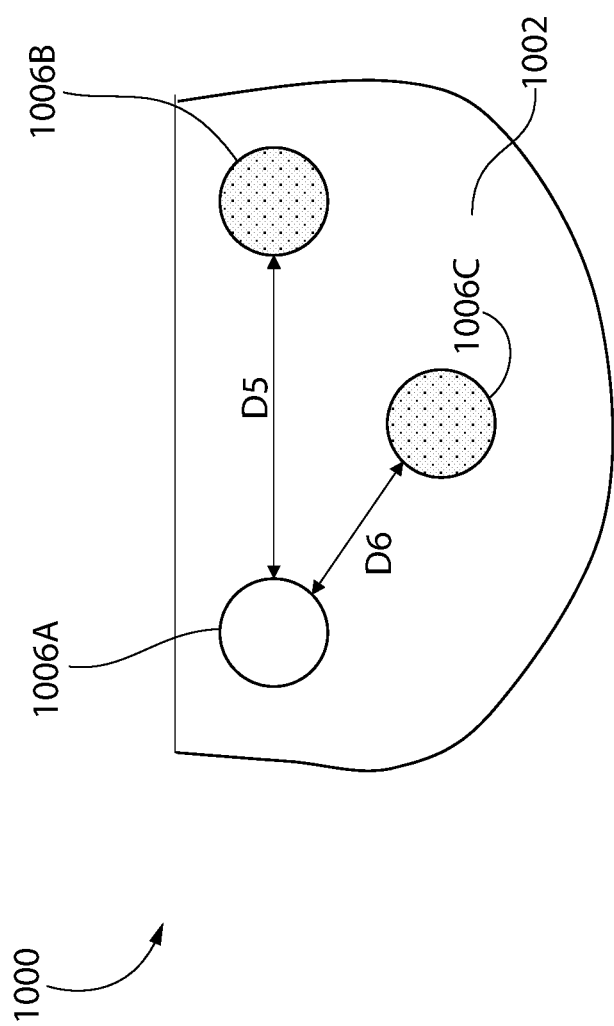
Figure 11:
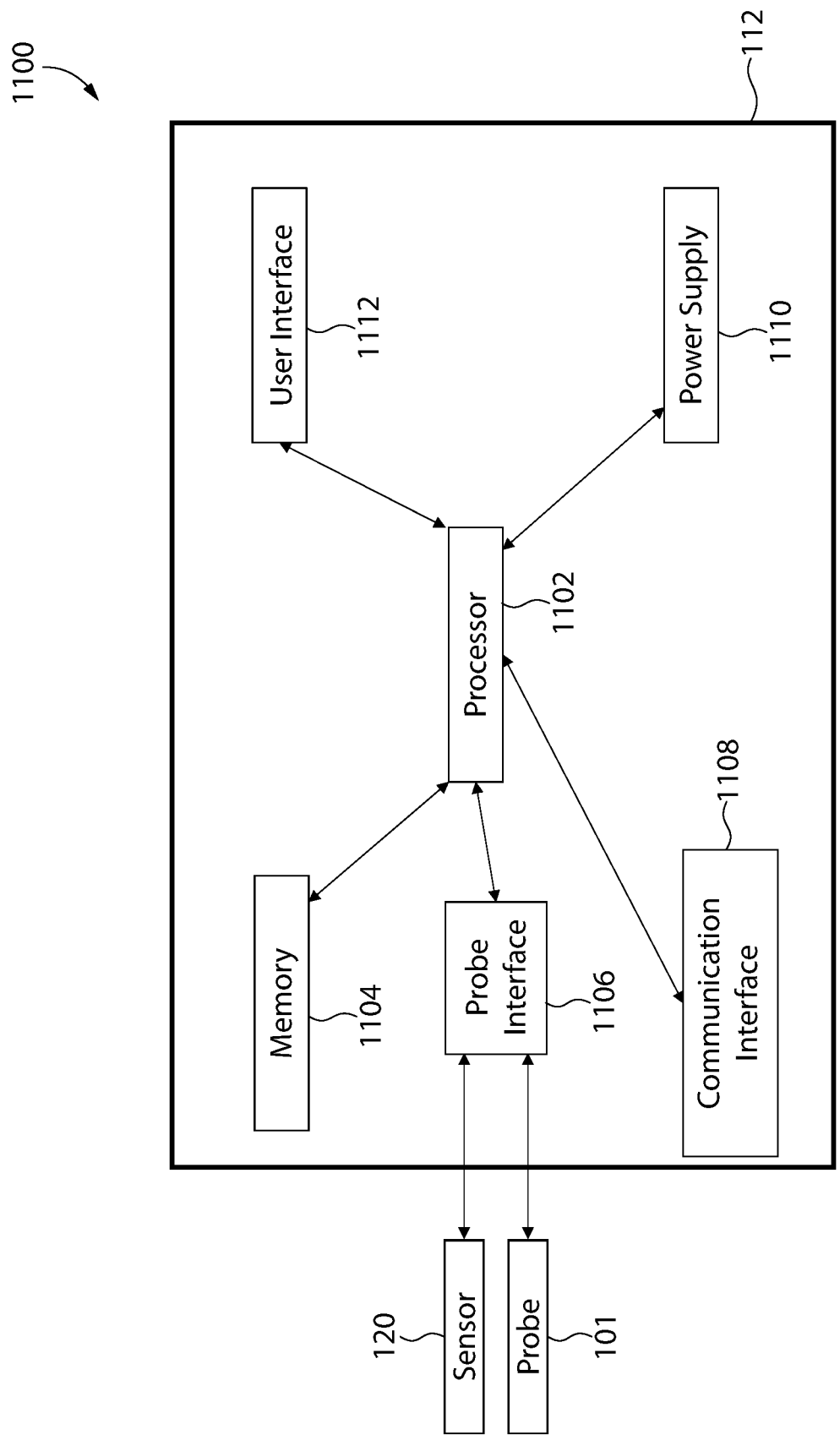
Figure 12:
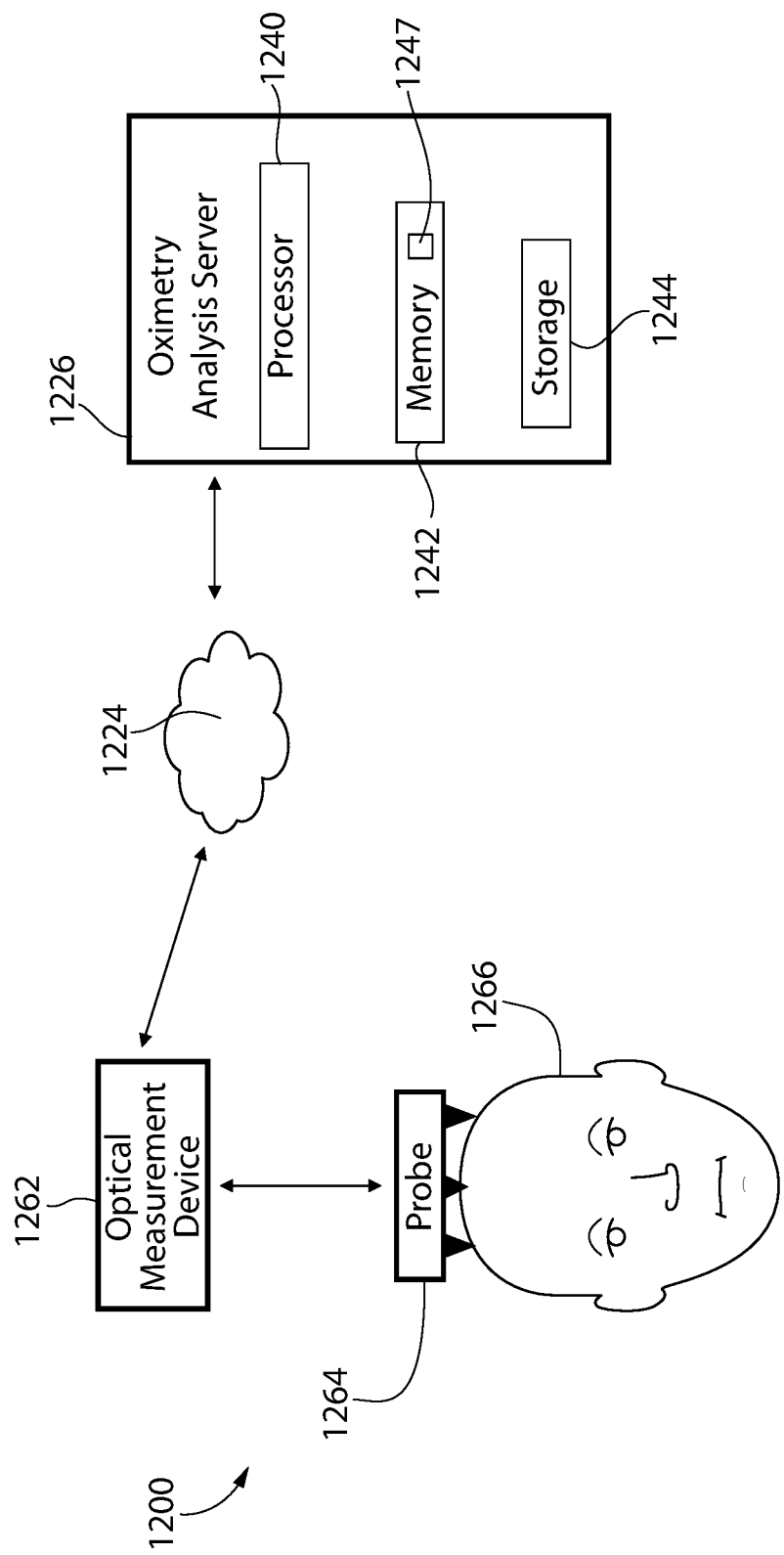
Figure 13:
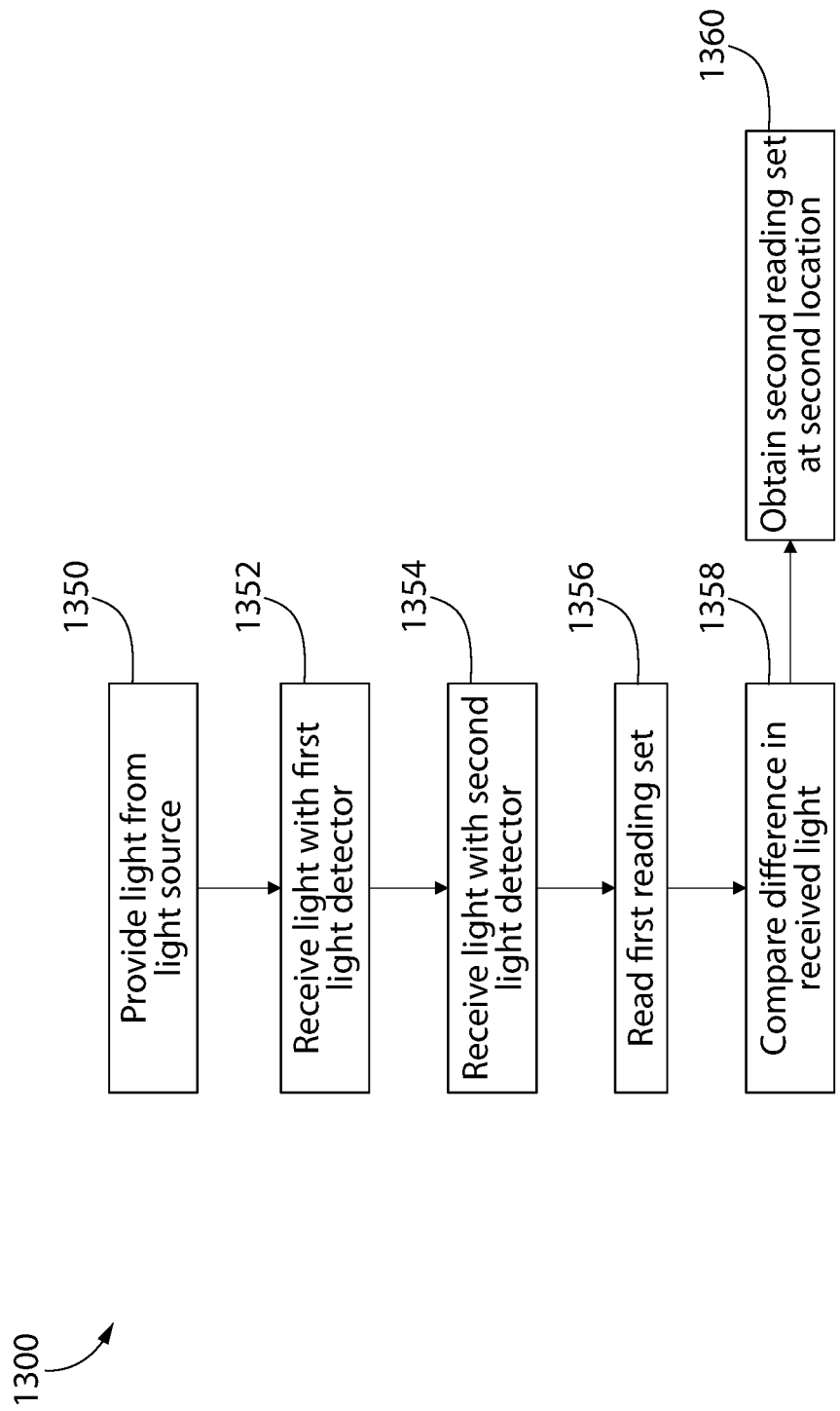
Figure 14:
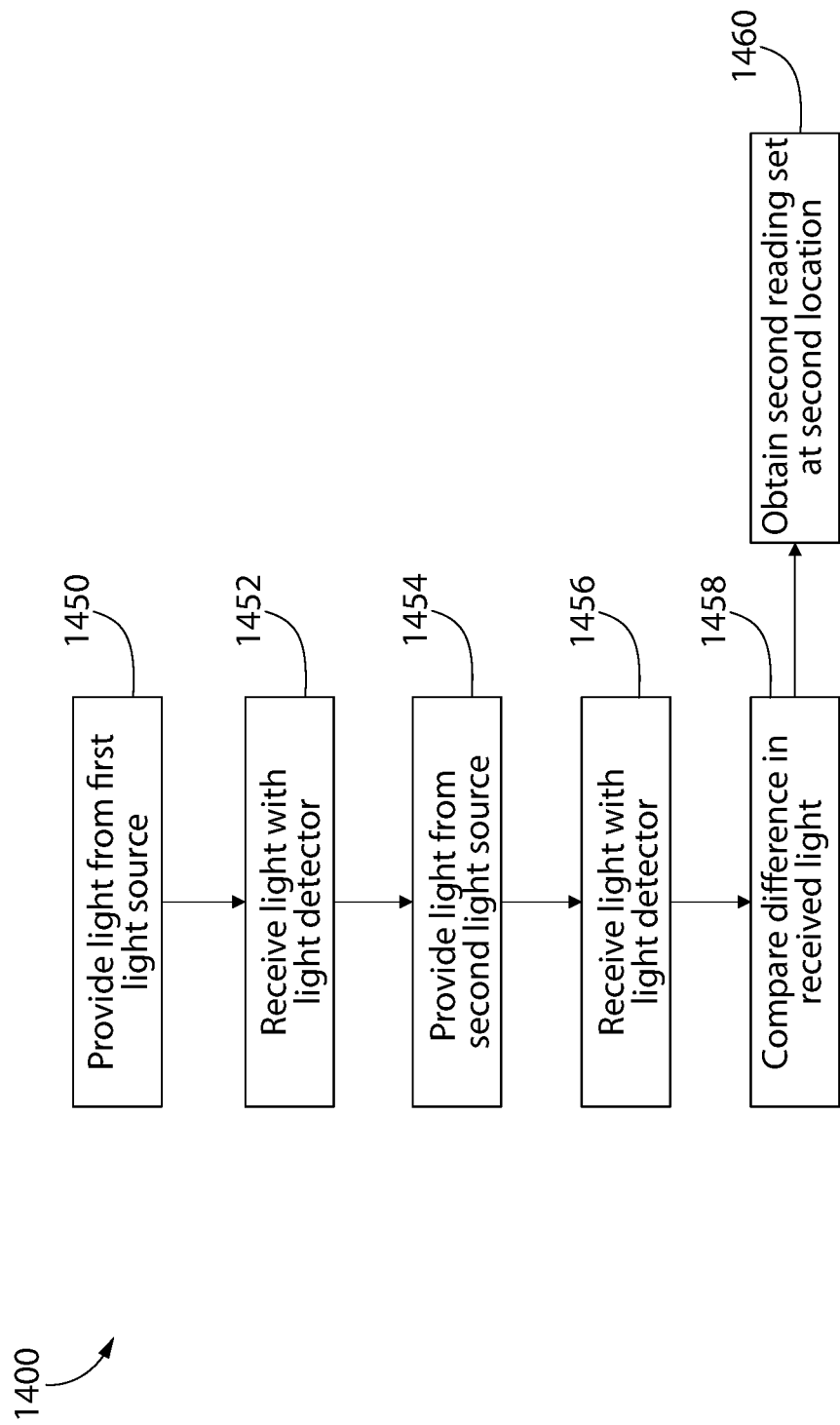
Figure 15A:
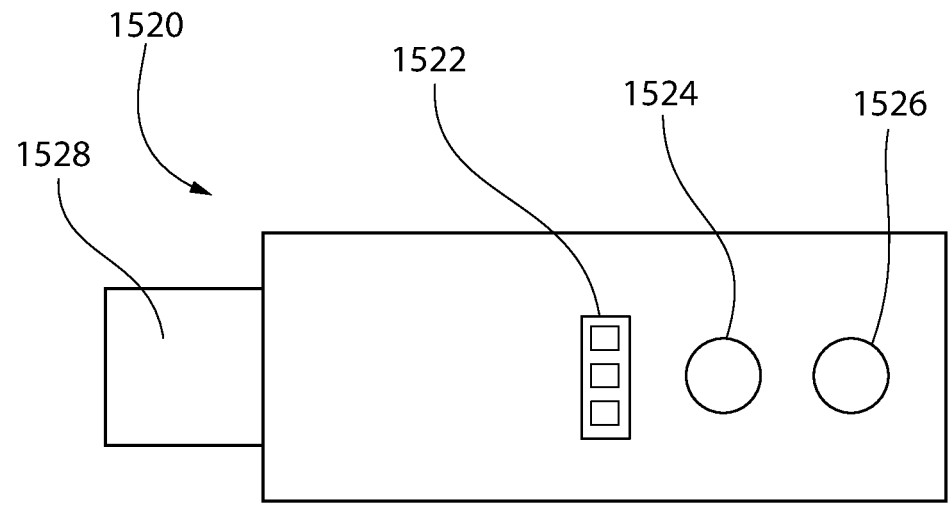
Figure 15B:
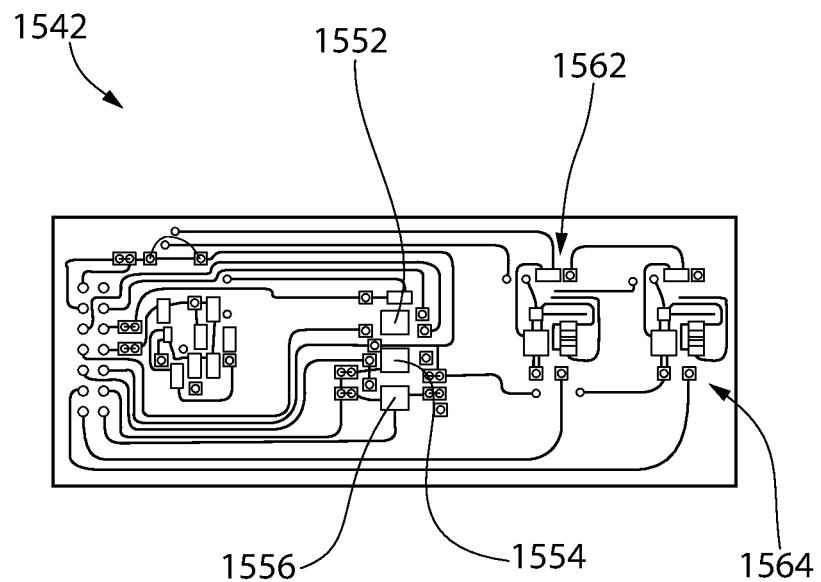

FIG. 7A is a side view of the optical probe of FIG. 4 having a conical shroud in accordance with embodiments of the present invention;

FIG. 7B is a top view of the conical shroud shown in FIG. 7A;

FIG. 8 is a side view of the optical probe of FIG. 4 having two conical shrouds in accordance with embodiments of the present invention;

FIG. 9 is a top view of an optical probe in accordance with embodiments of the present invention;

FIG. 10 is a top view of an optical probe in accordance with alternative embodiments of the present invention;

FIG. 11 is a block diagram of an optical probe used with embodiments of the present invention;

FIG. 12 is a schematic of an embodiment of the present invention utilizing remote analysis;

FIG. 13 is a flowchart indicating process steps for an embodiment of the present invention;

FIG. 14 is a flowchart indicating process steps for an alternative embodiment of the present invention;

FIG. 15A is a sensor for use with an optical probe system according to an embodiment of the present invention; and FIG. 15B is to top plan view of a circuit of the sensor shown in FIG. 15A.

DETAILED DESCRIPTION OF THE INVENTION

The probe of the present invention in some embodiments, as discussed in further detail below, may include one or more light source(s) and one or more light sensor(s) for making an oximetry measurement used to detect a brain trauma in a patient. In some embodiments, the light sources are near infrared (NIR) light sources, providing light with wavelengths ranging from 600 nanometers to 1000 nanometers. The use of infrared spectroscopy can be invaluable for assessing head trauma in situ, using portable equipment. It allows a diagnosis to be performed at or near the location where an injury occurred. Disclosed embodiments of the invention may utilize a disposable cover attachment with a three-point triangular configuration. This triangular configuration may provide for reliable contact against a human head for performing the measurements. Additionally, embodiments disclosed herein may utilize a shroud for each light source, reducing unwanted reflections, and improving the accuracy and reliability of readings.

Referring to the drawings in detail, wherein like reference numerals indicate like elements throughout, there is shown in FIGS. 1-15B an optical probe 101 and a diagnostic system, generally designated 103, exemplary embodiments of the present invention. Various embodiments of the optical probe 101 and diagnostic system 103 are described in further detail below in reference to the exemplary embodiments shown in the figures.

Figure 1:
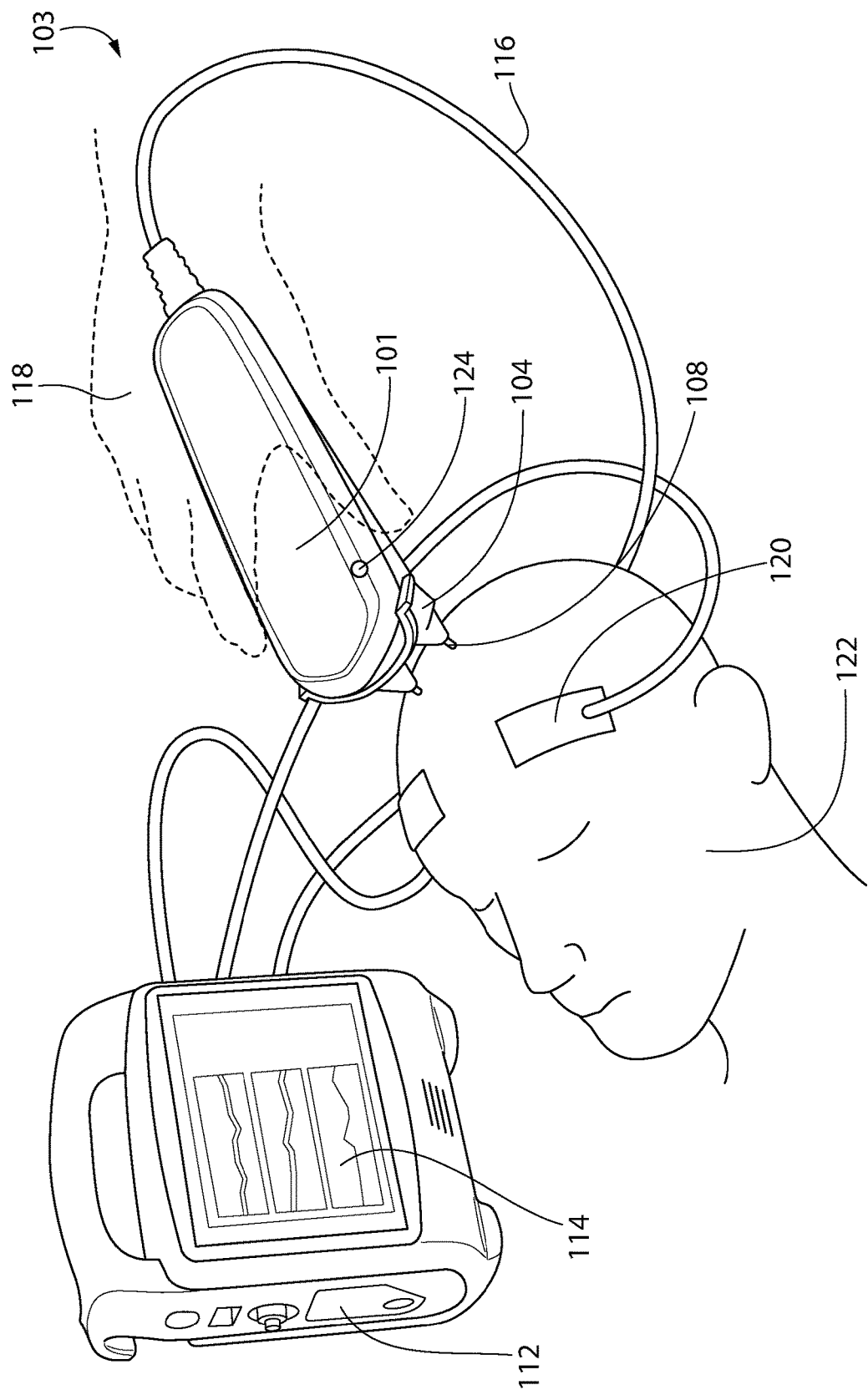

FIG. 1 shows an example of a diagnostic system 103 in use on a head 122 of a patient. The probe 101 is configured to be grasped and operated by a single hand 118 of the user. The probe 101 includes a plurality of optical elements 108 that extend from the probe and are applied to a patient's head 122. A user may use his/her hand 118 to place the optical fibers 108 extending from the probe 101 at a desired location on the head 122 of a patient. Preferably the optical fibers 108 extend between the patient's hairs to directly contact the user's scalp.

Referring to FIGS. 2A and 2B, the probe 101 includes three optical elements 153, 155, 157 including one or more light source(s) and one or more light sensor(s), or two light sensors with a single light source. In one embodiment, the three optical elements 153, 155, 157 are positioned in a triangular configuration. Three optical fibers 108A, 108B, 108C may be provided and each coupled to one of the three optical elements 153, 155, 157 and having an exposed distal end portion 108D.

The distal end of the optical probe may include a cover 104 having a housing 102 and including the three optical elements 153, 155, 157. In some embodiments, cover 104 is removably attached to the base 101a, the remainder of the optical probe 101. The cover 104 may be removably attached to the base 101a via a snap fit or a fastener such as a screw or magnet. In one embodiment, the cover 100 includes a pair of flexible diametrically opposed tabs or handles 104a extending laterally from the cover 104 and configured to snap fit onto the base 101a. Handles 104a may be affixed to housing 102 to facilitate easy installation and removal from the optical probe from the base 101a. The handles 104a may flex outwardly from the cover 104 to aid in snapping onto the base 101a. In one embodiment, the base 101a includes a corresponding rib, lip, groove or other feature configured to engage the handles 104a to retain the cover 104 to the base 101a.

In use, the cover 104 may be a disposable item, used for a single patient, and then discarded, while the base 101a houses the electronics and other reusable components and is used for multiple patients. In other embodiments, the cover 104 is fixed to the base 101a. In such embodiments, a removeable protective transparent cap (not shown), shaped generally to the contour of the cover 104, may be used and disposed between each patient. The part touching the patient is designed as disposable, so it can be replaced between patients. Having a removable cover or cap that can be disposed allowing reuse of the base may help to maintain sanitary conditions for the patient during use of the probe and allow for the base housing the more expensive electronics to be reused.

Three bosses, indicated as 106A, 106B, and 106C may project from the housing 102 and be disposed around a portion of an optical fiber. The three optical fibers 108A, 108B, and 108C have light-transmitting properties, and are also substantially rigid, such that they hold their shape when pressed against a human head during analysis. The optical fibers 108A, 108B, and 108C may be comprised of glass or an optically transparent plastic material. In one embodiment, the optical fibers 108A, 108B, and 108C are comprised of an acrylic glass such as poly(methly methacrylate) (PMMA). In some embodiments, the optical fibers each have a diameter ranging from half of a millimeter to three millimeters. In a particular embodiment, each optical fiber has a diameter of 1.5 millimeters. In one embodiment, each optical fiber extends orthogonally from a housing of the removable cover and are generally parallel to one another.

In the embodiment shown, boss 106A is disposed around optical fiber 108A, boss 106B is disposed around optical fiber 108B, and boss 106C is disposed around optical fiber 108C. A distal end portion of each optical fiber 108A, 108B, 108C may extend from the end of each boss 106A, 106B, 106C. In one embodiment, the bosses 106A, 106B and 106C are conical or frusto-conical in shape. In one embodiment, the bosses 160A, 106B and 106C tapper toward the exposed optical fiber. In other embodiments, the bosses 106A, 106B and 106C are pyramid, rectangle or other desired shapes. In one embodiment, each boss 106A, 106B and 106C are each generally the same shape and size as one another. In other embodiments, the bosses 106A, 106B and 106C are sized and/or shaped differently from one another.

Figure 2D:
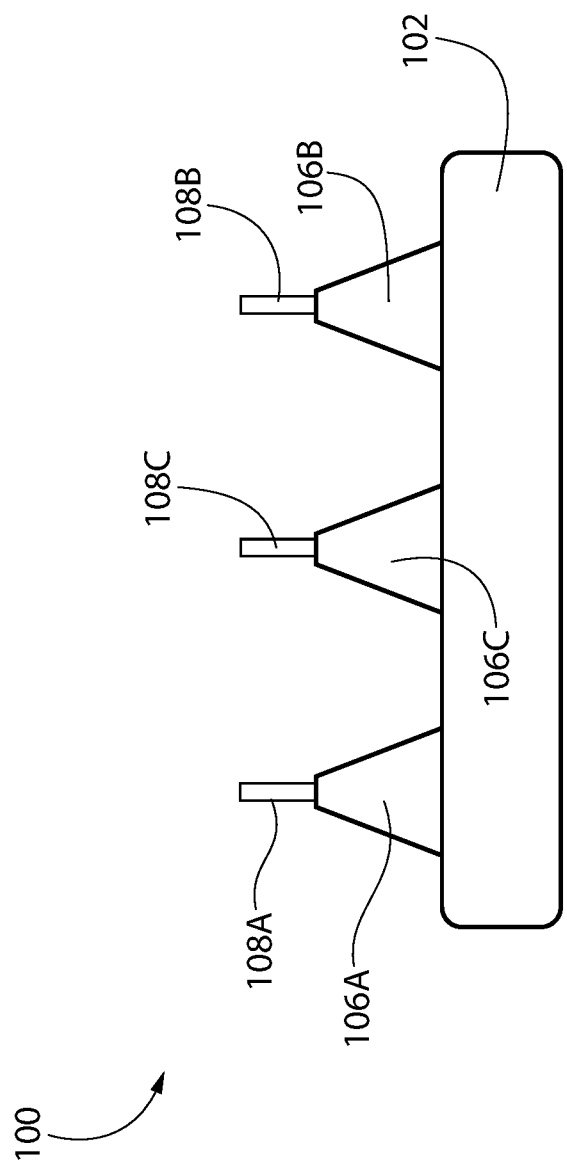

Referring to FIGS. 2C and 2D, the distance between optical fiber 108A and optical fiber 108B is indicated as D1. The distance D1 may be approximately 3-5 cm. In one embodiment, the distance D1 is approximately 4 cm. The distance between optical fiber 108A and optical fiber 108C is D2. The distance D2 may be approximately 2-4 cm. In one embodiment, the distance D2 is approximately 2.5 cm. In some embodiments, D1 is greater than D2. In one embodiment, the distances D1 and D2 corresponds to distances between light sources and/or light detectors on the probe. In other embodiments, the distances D1 and D2 are different than the distances between light sources and/or light detectors on the probe such that the cover 104 alters the distances to a preferred distance and allows for different covers 104 to provide different predetermined distances. The difference in distances between a light source and a light detector may be used in determining if a head trauma is a scalp trauma (hematoma above the skull, i.e. skin hematoma) or an intracranial trauma.

Figure 3A:
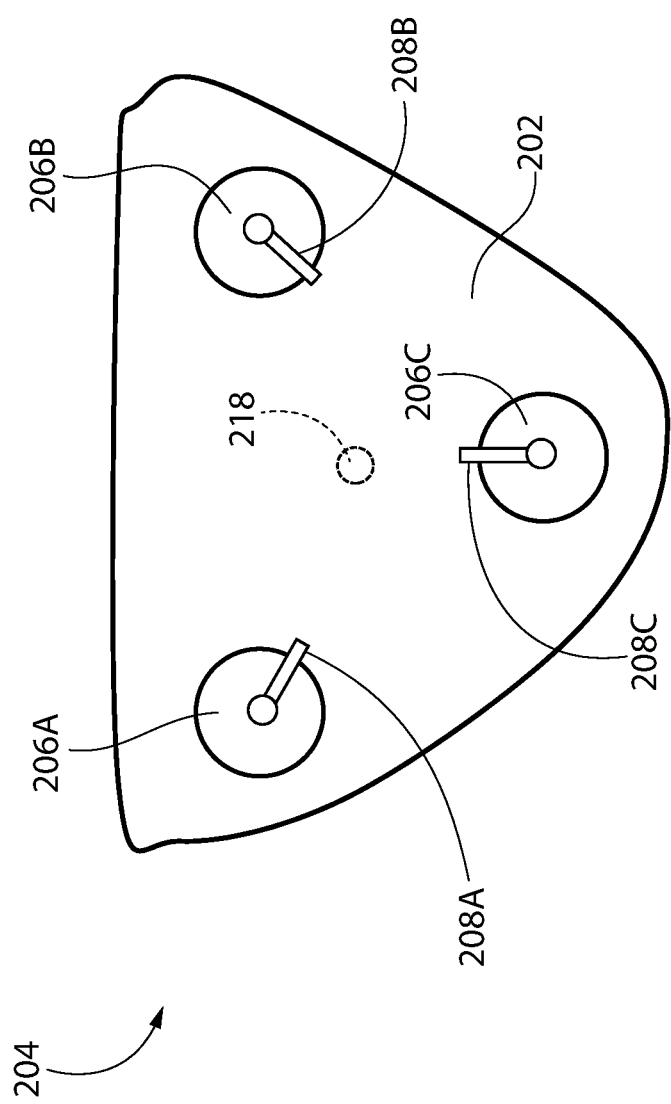

FIG. 3A is a top view a cover 204 in accordance with alternative embodiments of the present invention. Cover 204 includes bosses 206A, 206B, and 206C, each surrounding a respective optical fiber 208A, 208B, and 208C. Cover 200 is similar to cover 104 shown in FIGS. 2A-2D, with a difference being that each optical fiber is bent inwards at an angle towards a central point 218 of the housing 202.

FIG. 4 shows an example of potential interference between optical fibers. The interference may inhibit the ability to make a distinction between a scalp trauma and an intracranial trauma. In some tissue oximetry methods, several detectors are used at different source-detector separations to measure a different tissue volume at a different geometry. The minimalist continuous wave (CW) tissue oximetry methods use multi-wavelength light source and two detectors aligned in a line with two source detector separations. For use on the head, in areas covered by hair, those probes do not work well, as human hair absorbs NIR light and no signal can be measured through hair. Disclosed embodiments use a probe cover such as that shown in FIGS. 1-3 that utilize optical fibers in a "hairbrush" like arrangement to penetrate through the hair and reach directly to the scalp through hair.

By performing measurements at two different source-detector separations, measurements may be easily performed with different combinations of superficial and/or deeper brain tissue. A basic method for detection of brain hematomas includes measurement of at least two symmetrical head locations, and detecting a difference between the ipsilateral and the contralateral sides of the head.

Disclosed embodiments may utilize a probe that can be used for both brain oximetry, and an evaluation of scalp/intracranial traumas. The probe may include at least two source-detector separations. The signal of the detector closer to the light source may be influenced mostly by the skin and superficial tissues, while the signal of the detector farther from the light source may be influenced mostly by the deeper tissues. From those two signals and their comparison to the signals measured at the other side of the head, disclosed embodiments determine if the hematoma is intracranial or originates in the skin.

Figure 3B:
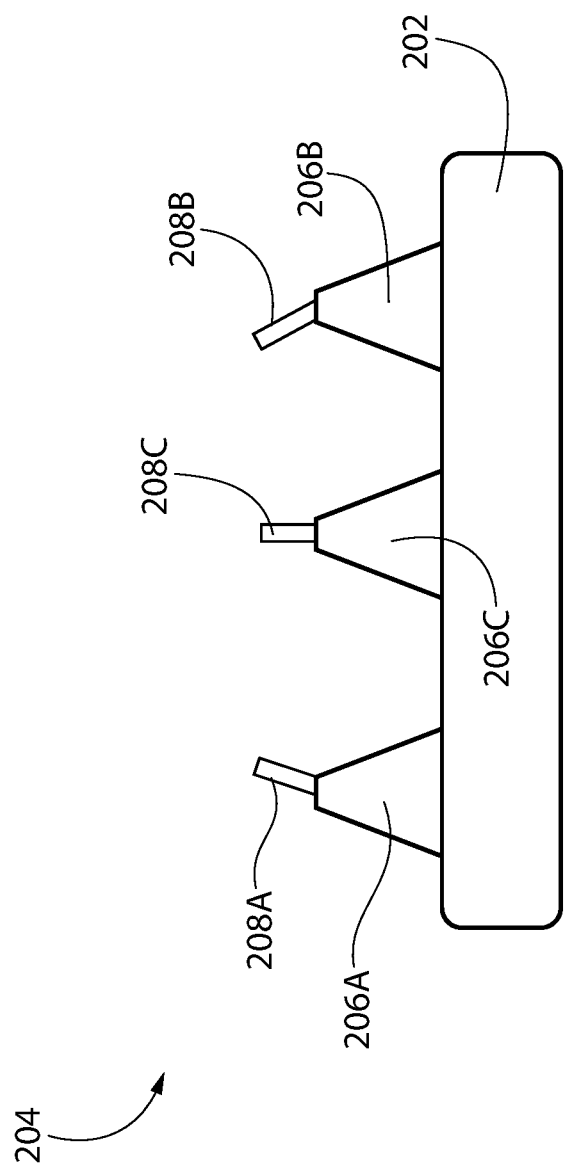

As shown in FIG. 4, cover 104 is disposed on probe 151, which is being applied to a human head region 140. Probe 151 includes a light source 153, a first light detector 155, and a second light detector 157. As shown in FIG. 3, the cover 100 is shown in cutaway where the optical fibers are indicated as traversing through their respective bosses and the housing 102 to the corresponding optical element, where the optical element can be a light source or a light detector. The light from the light source 153 is oriented such that light travels through optical fiber 108A, and is received by both optical fiber 108B via light path P1, and also received by optical fiber 108C via light path P2. Optical fiber 108B provides light to light detector 155, and optical fiber 108C provides light to light detector 157. A portion of the light output from light source 153 is reflected off the tissues of head region 140, as indicated by light path P3. Light path P3 represents unwanted interference. Some of the light from path P3 can enter optical fiber 108B and optical fiber 108C, and enter the respective light detectors 155 and 157. This can adversely affect measurements of the difference in light intensity detected by light detector 155 and light detector 157, since the light originating from path P3 is not passing through the tissues of head region 140.

Figure 5B:
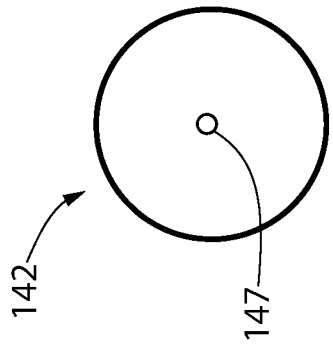
Figure 5A:
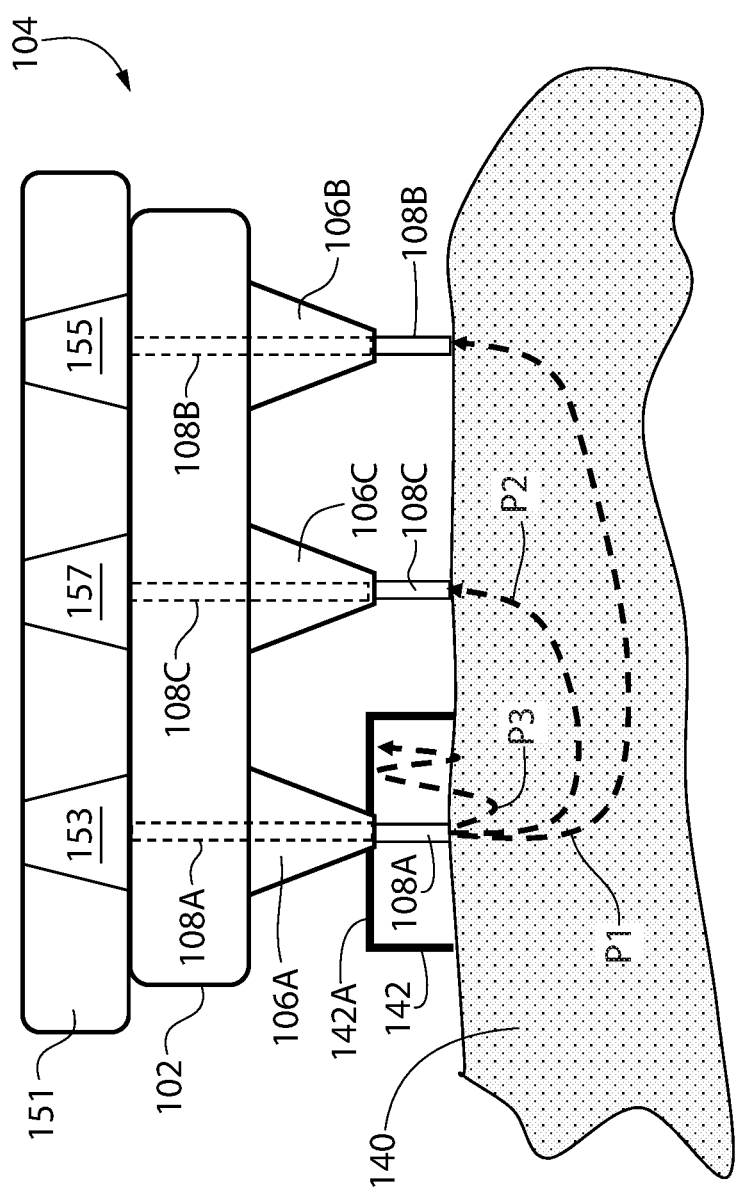

FIGS. 5A and 5B show an example usage of a light shield or shroud 142 in accordance with embodiments of the present invention to prevent unwanted interference as discussed above. At least one light shroud 142 may be provided to reduce interference. In one embodiment, the light shroud 142 is disposed radially around the exposed distal end portion of the optical fiber 108A coupled to the at least one light source 153. In one embodiment, shroud 142 is generally cylindrical in shape. In one embodiment, shroud 142 is cylindrical or any other shape outwardly but forms a cylindrically shaped space shrouded radially from the exposed distal tip of the optical fiber.

Shroud 142 is shown in a cross-sectional view and is placed around the optical fiber 108A corresponding to light source 153. Shroud 142 may include an opening 147 (see FIG. 5B) configured to allow optical fiber 108A to pass through. In some embodiments, the shroud 142 may be held in place via a friction fit between opening 147 and optical fiber 108A. In other embodiments, the shroud 142 is friction or snap fit to the boss 106A. In other embodiment, the shroud 142 is removably attached to the housing 102. In other embodiments, the shroud 142 is non-removably attached to the optical fiber 108A, boss 106A or housing 102. In other embodiments, the housing 102 and/or boss 106A is shaped to at least partially form the shroud 142. The shroud 142 is preferably comprised of or includes on an outwardly facing surface a non-reflective, light-absorbing member 142A, such as felt, matte base material finish or coating, or other suitable material. In some embodiments, the light-absorbing member 142A and/or inwardly facing surface of the shroud 142 is black in color.

Referring to FIG. 5A with comparison to FIG. 4, it can be seen that light path P3 does not travel beyond the shroud 142 (or is at least partially blocked), and thus reduces interference with the intensity measurements from light detector 155 and light detector 157. With this arrangement, the light reaching the detectors 155 and 157 is at least mostly light that traveled through the tissue of head region 140, enabling a more accurate determination of scalp injuries and intracranial injuries. In some embodiments, the cover 104 comprises a first optical fiber covering the first light detector, a second optical fiber covering the second light detector, and a third optical fiber covering the light source.

Figure 6:
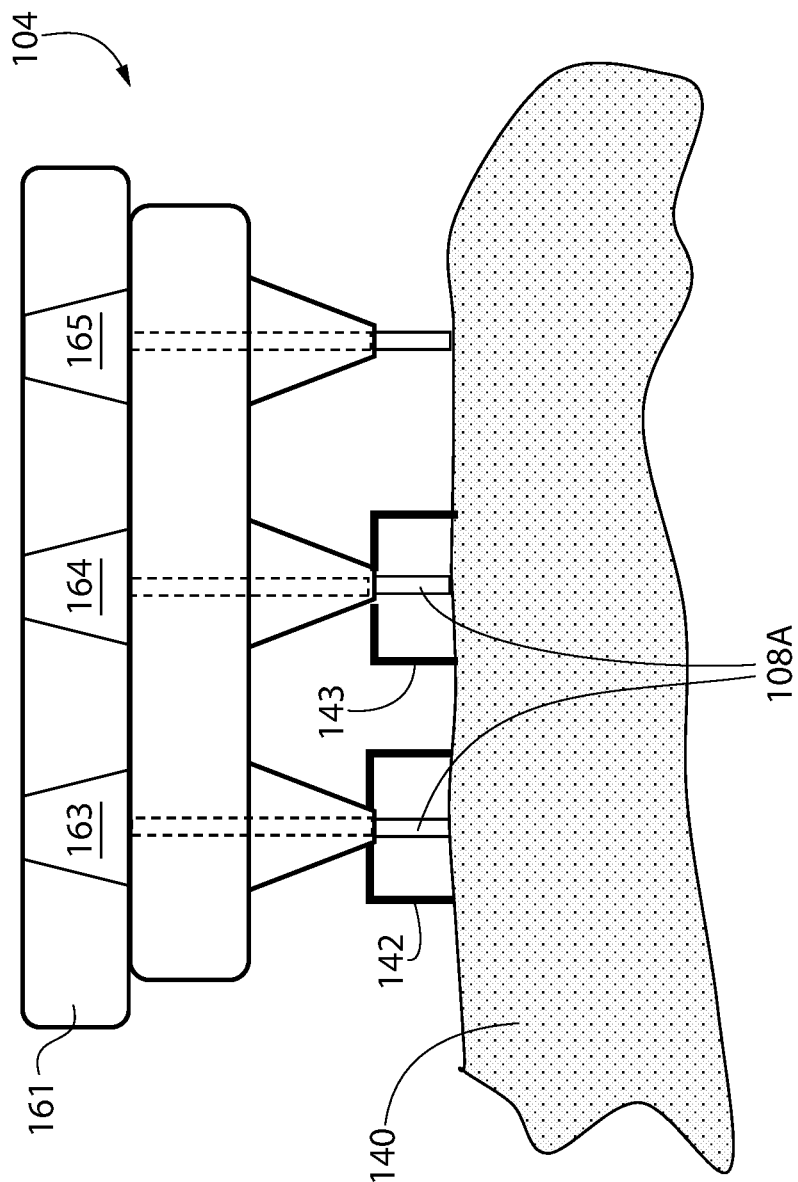

FIG. 6 shows an example of dual shrouds in accordance with embodiments of the present invention. Shroud 143 is similar to cylindrical shroud 142, which is also illustrated in FIG. 5A and FIG. 5B. This embodiment is used with a probe 161 comprising two light sources (163 and 164), and a single light detector 165. Thus, in this embodiment, two shrouds (142 and 143) are used, one corresponding to each light source. In embodiments, the cover 100 comprises a first optical fiber covering the first light source, a second optical fiber covering the second light source, and a third optical fiber covering the light detector. Embodiments include a first light shroud disposed around the first optical fiber and a second light shroud disposed around the second optical fiber.

FIG. 7A and FIG. 7B show an example of a conical shroud in accordance with embodiments of the present invention. In FIG. 7A, conical shroud 152 is shown in a cross-sectional view and is placed around the optical fiber 108A corresponding to light source 153. In one embodiment, shroud 142 is conical or any other shape outwardly but forms a frusto-conically shaped space shrouded radially from the exposed distal tip of the optical fiber.

FIG. 7B shows a top-down view of the conical shroud 152, indicating opening 159 for optical fiber 108A to pass through. In embodiments, the shroud 152 may be held in place via a friction fit between opening 159 and optical fiber 108A. Similar to the embodiment depicted in FIG. 5A, stray light from the light source 153 may be at least partially blocked by conical shroud 152.

FIG. 8 shows an example of dual conical shrouds in accordance with embodiments of the present invention. Conical shroud 156 is similar to conical shroud 152, which is also illustrated in FIG. 7A and FIG. 7B. This embodiment is used with a probe 161 comprising two light sources (163 and 164), and a single light detector 165. Thus, in this embodiment, two conical shrouds (152 and 156) are used, one corresponding to each light source. Embodiments include a first light shroud disposed around the first optical fiber and a second light shroud disposed around the second optical fiber. In other embodiments, the shroud(s) 142 are any desirable shape including triangular, rectangular, oval, or non-symmetrical. In some embodiments, the shroud 142 includes a continuous sidewall. In other embodiments, the shroud 142 is a non-continuous wall or protection that extends between two of the optical fibers. In one embodiment, shroud 142 includes one or more projections that are also configured to assist in combing hair out of the way.

Some embodiments include an optical tissue oxygenation measurement of the head (particularly in the near infrared (600-1000 nm) range) where the light source and the detector/s are connected to the measured tissue by optical fibers/ light guides. Some embodiments further include a method to differentiate between extracranial and intracranial hematomas. Using a detector placed at a short source-detector separation (1-2.5 cm) may allow for measurement of mostly extracranial hematomas, while a second detector placed at a longer source-detector separation (2.5 cm or more) may allow for measurement of both extracranial and intracranial hematomas. Using the signals of both source-detector paths, it is possible to deduce the location and classification (scalp or intracranial) of the hematoma.

FIG. 9 shows a top view of a probe 900 in accordance with embodiments of the present invention. Probe 900 includes three optical elements disposed within housing 902. The optical elements include a combination of light detector and light source elements, and the three optical elements are positioned in a triangular configuration. The triangular configuration may have a significant advantage over a linear configuration, in that with a substantially round shape of a human head, it is much easier to make contact with all three optical fibers against the head using the triangular configuration of disclosed embodiments, without the need for any moving parts pertaining to adjustment of optical fiber length/ position.

In this embodiment, the three optical elements comprise a first light detector, a second light detector, and a light source. Probe 900 may include a first light detector 906A, a second light detector 906C, and a light source 906B. Light source 906B is separated from light detector 906A by distance D3. Light source 906B is separated from light detector 904C by distance D4. In some embodiments, D3 is greater than D4. Thus, in some embodiments, the first light detector is disposed at a first distance from the light source, and the second light detector is disposed at a second distance from the light source, and the first distance is greater than the second distance.

In some embodiments, D3 has a value ranging between 2.5 centimeters and 6 centimeters. In some embodiments, D4 has a value ranging between 1 centimeter and 4 centimeters. In some embodiments, D3 is not equal to D4. The difference in distance values between D3 and D4 may allow for discerning of scalp versus intracranial trauma.

FIG. 10 shows a top view of a probe 1000 in accordance with alternative embodiments of the present invention. Probe 1000 includes three optical elements disposed within housing 1002. The optical elements may include a combination of light detector and light source elements, and the three optical elements are positioned in a triangular configuration. In this embodiment, three optical elements comprise a first light source, a second light source, and a light detector. Probe 1000 includes a first light source 1006B, a second light source 1006C, and a light detector 1006A. Light detector 1006A is separated from light source 1006B by distance D5. Light detector 1006A is separated from light source 1006C by distance D6. In some embodiments, D5 is greater than D6. Thus, in embodiments, the first light source is disposed at a first distance from the light detector, and the second light source is disposed at a second distance from the light detector, and the first distance is greater than the second distance.

In some embodiments, D5 has a value ranging between 2.5 centimeters and 6 centimeters. In some embodiments, D6 has a value ranging between 1 centimeter and 4 centimeters. In some embodiments, D5 is not equal to D6. The difference in distance values between D3 and D4 may allow for discerning of scalp versus intracranial trauma.

Referring to FIG. 1 the probe 101 is configured and sized to be grasped and operated by a single hand. The probe 101 includes a plurality of optical elements 108 that extend from the probe and are applied to a patient's head 122. Probe 101 may have a dual light detector configuration or a dual light source configuration as discussed above. The probe 101 may be connected wirelessly or via a cable 116 to an electronic monitoring device 112. Cable 116 may provide power and/or light to one or more electronic components within probe 101. A user may use his/her hand 118 to place the optical fibers 108 extending from the probe 101 at a desired location on the head 122 of a patient. Preferably the optical fibers 108 extend between the patient's hairs to directly contact the user's scalp. The user may then perform a measurement by activating a control on the user interface 114. In some embodiments, the user interface 114 may include a touch screen, such as a capacitive or resistive touch screen. In some embodiments, a control may be disposed on the probe 101, such as button 124, for initiating a measurement. During use, an operator may attempt to clean any blood from the head in the measurement area, to reduce its impact on the light measurements.

Thus, disclosed embodiments may provide a multifunction diagnostic system. The system may serve as a diagnosis, resuscitation, and surgery aid for traumatic brain injury and hemorrhagic shock patients using near-infrared spectroscopy (NIRS) technology. A current problem in trauma care, particularly for out-of-hospital trauma, is the lack of methods and systems to identify, monitor, and trend physiologic (biochemical, metabolic or cellular) parameters. Noninvasive devices to detect brain and body hemorrhage, edema, blood and tissue oxygen, and assess vital organ perfusion and cognitive function are desperately needed. Such technology provides critical baselines for monitoring and assessment of trauma victims resuscitation efforts and en route during evacuation. Disclosed embodiments may perform multiple monitoring and diagnostic functions in far forward field conditions.

Disclosed embodiments may further include additional sensors coupled to the electronic monitoring device, such as a sensor 120. In some embodiments, several different NIRS sensors 120 are placed on the head, torso, and/or on the limbs of the patient. Disclosed embodiments may enable multiple measurements in an integrated multifunction device, providing considerable weight and volume savings since many of the needed system elements are mutual (computer, screen, batteries, etc.).

In some embodiments, system 103 may perform multiple functions, including, but not limited to, full head scan for brain hematoma diagnosis (using probe 101), full head scan for local cerebral oximetry measurement (using probe 101), bilateral forehead cerebral oximetry/hypoxia monitoring (using sensor(s) 120), local tissue oximetry monitoring in extremities (using sensors similar to sensor(s) 120, placed on an extremity, like a leg or an arm), heart rate and heart rate variability ((using sensor(s) 120), respiration rate ((using sensor(s) 120), bilateral forehead cerebral edema monitoring ((using sensor(s) 120), and/or sedation monitoring in field surgery ((using sensor(s) 120).

The system 103 may help to avoid or at least reduce a patient's exposure to radiation by reducing the need for computed tomography (CT or CAT) scans to diagnose the patient with a brain trauma. Reducing the patient's exposure to radiation, in some embodiments, may have particular benefits in use with children or pregnant women where the exposure to radiation may be more detrimental as compared to non-pregnant adults. In some embodiments, the system 103 is configured for pediatric use.

FIG. 11 shows a block diagram 1100 of a device used with embodiments of the present invention. A processor 1102 is coupled to various components, including memory 1104. Memory 1104 may include a non-transitory computer readable medium such as random-access memory (RAM), static random-access memory (SRAM), read-only memory (ROM), flash, magnetic storage, optical storage, and/or other suitable storage technology. The memory 1104 may contain machine instructions, that when executed by processor 1102, perform steps in accordance with embodiments of the present invention. Processor 1102 may include one or more cores. Note that while one processor 1102 is shown in FIG. 11, in some embodiments, multiple processors may be used. The processors can include microprocessors, microcontrollers, digital signal processors (DSPs) and/or other suitable processors.

Block diagram 1100 further includes input/output (I/O) or probe interface 1106. The probe interface 1106 may include one or more pins configured to generate and/or receive signals from peripheral devices such as probe 1002 (FIG. 10) and/or sensor 1020 (FIG. 10).

Block diagram 1100 may further include communication interface 1108. Communication interface 1108 may include a wired and/or wireless Ethernet interface, a serial port, a USB (Universal Serial Bus) port, or other suitable mechanism for transmitting and receiving data and/or configuration information. Communication interface 1108 may include a cellular transceiver, near field communication (NFC) transceiver, Bluetooth™ transceiver, or other suitable transceiver to enable wireless communication. In embodiments, the processor 1102 communicates with remote computing devices via the Internet, by way of communication interface 1108. In some embodiments, the processor may transmit raw data, such as light intensity readings and measurement locations to a remote computing device for analysis. The remote computing device may then perform an analysis, and transmit results back to the processor 1102 for rendering on user interface 1112. In this way, computation-intensive operations can be performed on a remote device, reducing the computing and power requirements of the portable device (1000) used for in situ measurements.

User interface 1112 may include a screen or a touch screen such as a capacitive or resistive touch screen. User interface 1112 may include a keyboard, mouse or other suitable pointing device, joystick, one or more buttons, or other suitable mechanism to enable control of the device 1000 (FIG. 10).

Block diagram 1100 further includes power supply 1110. Power supply 1110 may include an AC (alternating current power supply), DC (direct current power supply), battery, or other suitable power source for providing power, enabling the portability of device 1000.

FIG. 12 shows an embodiment 1200 of the present invention utilizing remote analysis. Embodiment 1200 includes an optical measurement device 1262, which may be similar to device 1000 of FIG. 10, and contain components such as those indicated in block diagram 1100 of FIG. 11. Probe 1264, which may be similar to probe 1002 of FIG. 10 is applied to a patient 1266 at a variety of locations for taking measurements of light intensity. The probe 1264 may be in communication with measurement device 1262 via a wired connection such as shown in FIG. 10 with cable 1010. The wired connection may include multiple conduits for electrical and/or optical signals to travel to and from the probe and the optical measurement device. The optical measurement device, using a communication interface such as shown as 1108 in FIG. 11, communicates to an oximetry analysis server 1226 via network 1224. In embodiments, network 1224 may be the Internet, a wide area network (WAN), a local area network (LAN), or any other suitable network.

Oximetry analysis server 1226 may comprise processor 1240, memory 1242, and storage 1244. Instructions 1247 for executing embodiments of the present invention are shown stored in memory 1242. In some embodiments, the oximetry analysis server 1226 may perform an analysis of raw data acquired by probe 1264. The oximetry analysis server 1226 may then send results back to the optical measurement device 1262 and/or other electronic devices to report the results. In some embodiments the oximetry analysis server 1226 may be implemented in a cloud computing environment. In some embodiments, the oximetry analysis server 1226 may be implemented as a virtual machine operating in a cloud computing environment.

The embodiment 1200 depicted in FIG. 12 enables enhanced communication of results. In some embodiments, results of the oximetry measurements may be automatically sent via e-mail, text message, or other suitable mechanism to one or more persons on a distribution list, such as physicians and/or nurses, to quickly disseminate the trauma analysis information. In such embodiments, the optical measurement device 1262 may still perform some analysis locally, in the event that the optical measurement device is used in a situation where network 1224 is unavailable. In this way, the optical measurement device 1262 can operate in an offline mode, and still provide some trauma analysis results to the operator of the optical measurement device 1262.

FIG. 13 is a flowchart 1300 indicating process steps for an embodiment of the present invention. These steps are for a probe that includes one light source and two light detectors. In process step 1350, light is provided from the light source. In process step 1352, light is received by the first light detector. In process step 1354, light is received by the second light detector. In process step 1356, the reading set is recorded, such as in the memory 1104 (FIG. 11). The reading set includes a light intensity reading recorded by the first light detector and the second light detector. In process step 1358, the difference in received light between the two detectors is compared. Since the first light detector and second light detector are at different distances from the light source (see 800 of FIG. 8), the difference in reading can be used to evaluate the trauma as scalp or intracranial. In process step 1360, a similar reading is performed at a second location on the head of the patient. Thus, embodiments can include applying the optical probe to a second location on the human head; providing light from the light source; receiving light from the first light detector; receiving light from the second light detector; and recording the received light from the first light detector and the second light detector as a second reading set. In embodiments, the first location is on an ipsilateral side of the human head, and wherein the second location is on a contralateral side of the head.

Disclosed embodiments may enable the classification of a head trauma as a scalp trauma or an intracranial trauma. Some embodiments include determining a first intensity difference between light received by the first light detector in the first location and light received by the first light detector in the second location; determining a second intensity difference between light received by the second light detector in the first location and light received by the second light detector in the second location; wherein the hematoma is classified as an intracranial hematoma in response to detecting the first intensity difference as greater than the second intensity difference.

Some embodiments further include determining a first intensity difference between light received by the first light detector in the first location and light received by the first light detector in the second location; determining a second intensity difference between light received from the second light detector in the first location and light received from the second light detector in the second location; wherein the hematoma is classified as a scalp hematoma in response to detecting the second intensity difference as greater than the first intensity difference.

While measurements at two locations are depicted in flowchart 1300, in practice, more than two locations may be used in performing a head trauma analysis. In some embodiments, measurements are performed on the frontal, temporal, parietal and occipital regions of the head, for both the right and left sides of the head, for a total of eight measurements.

Disclosed embodiments may involve comparing left and right sides of the head, the left side is used for calibration for the right-side measurement. This may eliminate the need for absolute calibration with external material.

In some embodiments, if the larger difference between the left and right measurements is for the close distance measurement (e.g. D4 of FIG. 9 or D6 of FIG. 10), it indicates a head trauma classification of scalp hematoma. Similarly, if the larger difference between the left and right measurements is for the long-distance measurement (e.g. D3 of FIG. 9 or D5 of FIG. 10), it indicates a head trauma classification of intracranial hematoma. Some embodiments may utilize a ratio of the signals between the short and long detectors as an indicator of the head trauma classification type (scalp or intracranial).

In some embodiments, the process steps may be performed in a different order than what is depicted in flowchart 1300. In some embodiments, two or more process steps may be performed simultaneously. For example, process steps 1352 and 1354 may be performed simultaneously.

FIG. 14 is a flowchart 1400 indicating process steps for an alternative embodiment of the present invention. These steps are for a probe that includes two light sources and one light detector. In process step 1450, light is provided from the first light source. In process step 1452, light from the first light source is received by the light detector. In process step 1454, light is provided from the second light source. In process step 1456, light from the second light source is received by the light detector. In process step 1458, the difference in received light between the two light sources is compared. Since the first light source and second light source are at different distances from the light detector (see 900 of FIG. 9), the difference in reading can be used to evaluate the trauma as scalp or intracranial. In process step 1460, a similar reading is performed at a second location on the head of the patient.

Some embodiments include applying the optical probe to a second location on the human head; providing light from the first light source; providing light from the second light source; receiving light from the first light source at the light detector; receiving light from the second light source at the light detector; and recording received light emitted from the first light source and the second light source as a second reading set.

Some embodiments further include, determining a first intensity difference between light received from the first light detector in the first location and light received from the first light detector in the second location, determining a second intensity difference between light received from the second light source in the first location and light received from the second light source in the second location, and wherein the hematoma is classified as an intracranial hematoma in response to detecting the first intensity difference as greater than the second intensity difference.

Some embodiments further include, determining a first intensity difference between light received from the first light source in the first location and light received from the first light source in the second location; determining a second intensity difference between light received from the second light source in the first location and light received from the second light source in the second location; and wherein the hematoma is classified as a scalp hematoma in response to detecting the second intensity difference as greater than the first intensity difference.

While measurements at two probe locations are depicted in flowchart 1300 and flowchart 1400, in practice, more than two locations may be used in performing a head trauma analysis. In some embodiments, measurements are performed on the frontal, temporal, parietal and occipital regions of the head, for both the right and left sides of the head, for a total of eight measurements.

In some embodiments, the process steps may be performed in a different order than what is depicted in flowchart 1400. In some embodiments, two or more process steps may be performed simultaneously.

The light sources used in probes 900 and 1000, and in the methods depicted by flowcharts 1300 and 1400 may combine light of one or more wavelengths. In some embodiments, the light from the light sources may be pulsed. In some embodiments, the light sources may be pulsed at a rate ranging between 800 Hz and 1.5K Hz. In a particular embodiment, a pulse rate of 1 KHz is used.

In some embodiments, the light detectors used in probes 900 and 1000, and in the methods depicted by flowcharts 1300 and 1400 may utilize an amplifier and/or filtering techniques to enable the detector to receive the pulsed signals from the light source(s), while ignoring other light sources such as lamps that modulate in the 50 Hz-120 Hz range, thus improving the accuracy of measurements.

FIG. 15A shows detail of a sensor similar to sensor 120 of FIG. 1. In some embodiments, sensor 1520 includes multiple wavelength light sources and two optical detectors. FIG. 15A shows sensor 1520 with the side that faces the skin of the patient during use. Sensor 1520 may include opening 1522 for one or more light sources. Sensor 1520 may further include opening 1524 for a first light detector, and opening 1526 for a second light detector. The sensor 1520 may include a connector 1528 for coupling to the user interface 112.

FIG. 15B shows the internal circuitry of the sensor 1520 of FIG. 15A. Circuit board 1542 includes light sources 1552, 1554, and 1556. In embodiments, the light sources 1552, 1554, and 1556 are arranged linearly. Circuit board 1542 further includes first light detector 1562 and second light detector 1564. Second light detector 1564 is at a greater distance from the light sources than first light detector 1562.

Note that while the examples disclosed herein describe use on human subjects, disclosed embodiments may also be suitable for use on animals. Animals may have a different hair density than humans, in terms of number of follicles per square centimeter. In many cases, animals have a higher hair density than humans. Thus, for use on animals, a different optical fiber diameter may be used. In some embodiments, the optical fiber diameter used may range from 0.9 millimeter to 1.2 millimeters for animal applications.

As can now be appreciated, disclosed embodiments provide improvements in the technical field of oximetry measurements. The novel arrangement of sensors, and use of the readings obtained from the sensors enables a new level of diagnosis in the field. This provides potentially lifesaving information for first responders, physicians, and other caregivers for head trauma victims.

Reference throughout this specification to "one embodiment," "an embodiment," "some embodiments", or similar language means that a particular feature, structure, or characteristic described in connection with the embodiment is included in at least one embodiment of the present invention. Thus, appearances of the phrases "in one embodiment," "in an embodiment," "in some embodiments", and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents.

In one embodiment, the includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a," "an" and "the" are not limited to one element but instead should be read as meaning "at least one."

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. An optical probe comprising:
   three optical elements including at least one light source and at least one light detector, the three optical elements being positioned in a triangular configuration;
   three optical fibers each coupled to one of the three optical elements and each having an exposed distal end portion; and
   at least one light shroud having an inner surface disposed radially around and spaced from the exposed distal end portion of at least one of the optical fibers coupled to the at least one light source,
   wherein the at least one light shroud comprises an opening that the at least one of the optical fibers extends through,
   wherein a distal tip of the exposed distal end portion of the one of the three optical fibers extending through the opening of the at least one light shroud is approximately on the same plane as a distal edge of the at least one light shroud.

2. The optical probe of claim 1 further comprising:
   a base housing the three optical elements; and
   a cover removably coupled to a distal end of the base, the cover including the three optical fibers.

3. The optical probe of claim 2, wherein the cover includes three bosses, each boss projecting from the cover and covering a portion of one of the three optical fibers.

4. The optical probe of claim 3, wherein each boss is frusto-conical in shape.

5. The optical probe of claim 2, wherein the cover includes at least one flexible tab extending laterally from the cover and configured to snap fit onto the base.

6. The optical probe of claim 1, wherein the three optical elements include a first light source, a second light source, and a light detector.

7. The optical probe of claim 6, wherein the at least one light shroud includes a first light shroud disposed around the exposed distal end portion of one of the optical fibers coupled to the first light source and a second light shroud disposed around the exposed distal end portion of one of the optical fibers coupled to the second light source.

8. The optical probe of claim 6, wherein the first light source is disposed at a first distance from the light detector, and wherein the second light source is disposed at a second distance from the light detector, and wherein the first distance is greater than the second distance.

9. The optical probe of claim 1, wherein the three optical elements include a first light detector, a second light detector, and a light source.

10. The optical probe of claim 9, wherein the first light detector is disposed at a first distance from the light source, and wherein the second light detector is disposed at a second distance from the light source, and wherein the first distance is greater than the second distance.

11. The optical probe of claim 10, the first light detector is configured to allow for measurement of extracranial hematomas and the second light detector is configured to allow for measurement of intracranial hematomas.

12. The optical probe of claim 1, wherein the three optical fibers are generally parallel to one another.

13. The optical probe of claim 1, wherein each of the three optical fibers extend at an angle towards a central point between the three optical fibers.

14. The optical probe of claim 1, wherein the at least one light shroud is cylindrically shaped.

15. The optical probe of claim 1, wherein the at least one light shroud is frusto-conically shaped.

16. The optical probe of claim 1, wherein the at least one light shroud includes a light-absorbing member disposed on an inside surface of the at least one light shroud comprised of a material different than a material of a remainder of the at least one light shroud.

17. The optical probe of claim 16, wherein the material of the light-absorbing member is configured to absorb more light than the material of the remainder of the at least one light shroud.

18. The optical probe of claim 1, wherein the distal tip of the exposed distal end portion of one of the three optical fibers extending through the opening of the at least one light shroud is on the same plane as the distal edge of the at least one light shroud.

19. The optical probe of claim 1, wherein an open space is formed between the inner surface of the at least one light shroud and the exposed distal end portion.

20. The optical probe of claim 19, wherein the open space is formed as a toroid or tube shape.

21. An optical probe comprising:
   a base housing three optical elements including at least one light source and at least one light detector, the three optical elements being positioned in a triangular configuration;
   a cover removably coupled to the base and including three optical fibers each coupled to one of the three optical elements and each having an exposed distal tip, the cover including three bosses, each boss projecting from the cover and covering a portion of one of the optical fibers; and
   at least one light shroud comprising:
   an opening, and
   a light-absorbing layer disposed on an inside surface of the at least one light shroud, the light-absorbing layer comprised of a material configured to absorb more light than a material of a remainder of the at least one light shroud, wherein the at least one light shroud is coupled to a distal end of one of the three bosses and disposed around the exposed distal tip of one of the optical fibers.

22. The optical probe of claim 21, wherein the light-absorbing layer is a felt or a matte base material finish or coating.

* * * * *